(12) United States Patent
Jin et al.

(10) Patent No.: US 7,542,574 B2
(45) Date of Patent: Jun. 2, 2009

(54) GENERATION OF CUSTOMISED THREE DIMENSIONAL SOUND EFFECTS FOR INDIVIDUALS

(75) Inventors: Craig Jin, Heathcote (AU); Philip Leong, Kowloon Tong (HK); Johahn Leung, Sydney (AU); Simon Carlile, Haberfield (AU); Andre Van Schaik, Glebe (AU)

(73) Assignee: Personal Audio PTY Ltd, Sydney NSW (AU)

( * ) Notice: Subject to any disclaimer, the term of this patent is extended or adjusted under 35 U.S.C. 154(b) by 22 days.

(21) Appl. No.: 11/736,553

(22) Filed: Apr. 17, 2007

(65) Prior Publication Data

US 2007/0183603 A1 Aug. 9, 2007

Related U.S. Application Data

(63) Continuation of application No. 10/181,648, filed on Dec. 12, 2002, now Pat. No. 7,209,564.

(30) Foreign Application Priority Data

Jan. 17, 2000 (AU) .................................... PQ5140

(51) Int. Cl.
*H04R 5/00* (2006.01)
(52) U.S. Cl. ........................................................ 381/17
(58) Field of Classification Search ............. 381/17–18, 381/310, 374, 370–371, 74, 322, 309, 312, 381/60–61; 600/559; 700/275; 703/1
See application file for complete search history.

(56) References Cited

U.S. PATENT DOCUMENTS 5,487,012 A * 1/1996 Topholm et al. ............ 700/163

(Continued)

FOREIGN PATENT DOCUMENTS

DE 19910372 A1 * 3/1999

(Continued)

*Primary Examiner*—Vivian Chin
*Assistant Examiner*—Lun-See Lao
(74) *Attorney, Agent, or Firm*—Greenberg Traurig, LLP

(57) ABSTRACT

A system for customising the synthesis and generation of spatial hearing in virtual auditory space (VAS) for individual listeners includes a measuring ruler (12) and a digital processing unit (DPU) (14) to which the ruler (12) is connected. The ruler (12) is used for measuring various physical dimensions of the morphology of a person's external auditory periphery (16). The ruler (12) comprises a base (18) insertable into an ear canal (20) of the person's ear. A robotic measuring arm (22) extends from the base (18) and has a measuring tip (24) to enable the ruler (12) to record the Cartesian (x,y,z) coordinates of the tip (24) relative to the base (18). By suitable manipulation of the robotic arm (22), the tip (24) can be positioned at desired locations on the person's external auditory periphery (16) to enable the morphological measurements of the person's external auditory periphery (16) to be effected. The ruler (12) is electrically connected via a lead (26) to the DPU (14) which is programmed to compute either head related transfer function (HRTF) filter coefficients or HRTF spectral weights. Functional relationships may thus be used to generate, by means of the DPU (28), HRTFs at any location for any individual listener given an encoding of the individual listener's morphological measurements.

21 Claims, 1 Drawing Sheet

U.S. PATENT DOCUMENTS

| | | | | |
|---|---|---|---|---|
| 5,742,689 | A * | 4/1998 | Tucker et al. | 381/17 |
| 6,996,244 | B1 | 2/2006 | Slaney et al. | |
| 7,209,564 | B2 * | 4/2007 | Jin et al. | 381/17 |

FOREIGN PATENT DOCUMENTS

| | | |
|---|---|---|
| WO | WO 97/25834 | 7/1997 |
| WO | WO 99/31938 | 6/1999 |

* cited by examiner

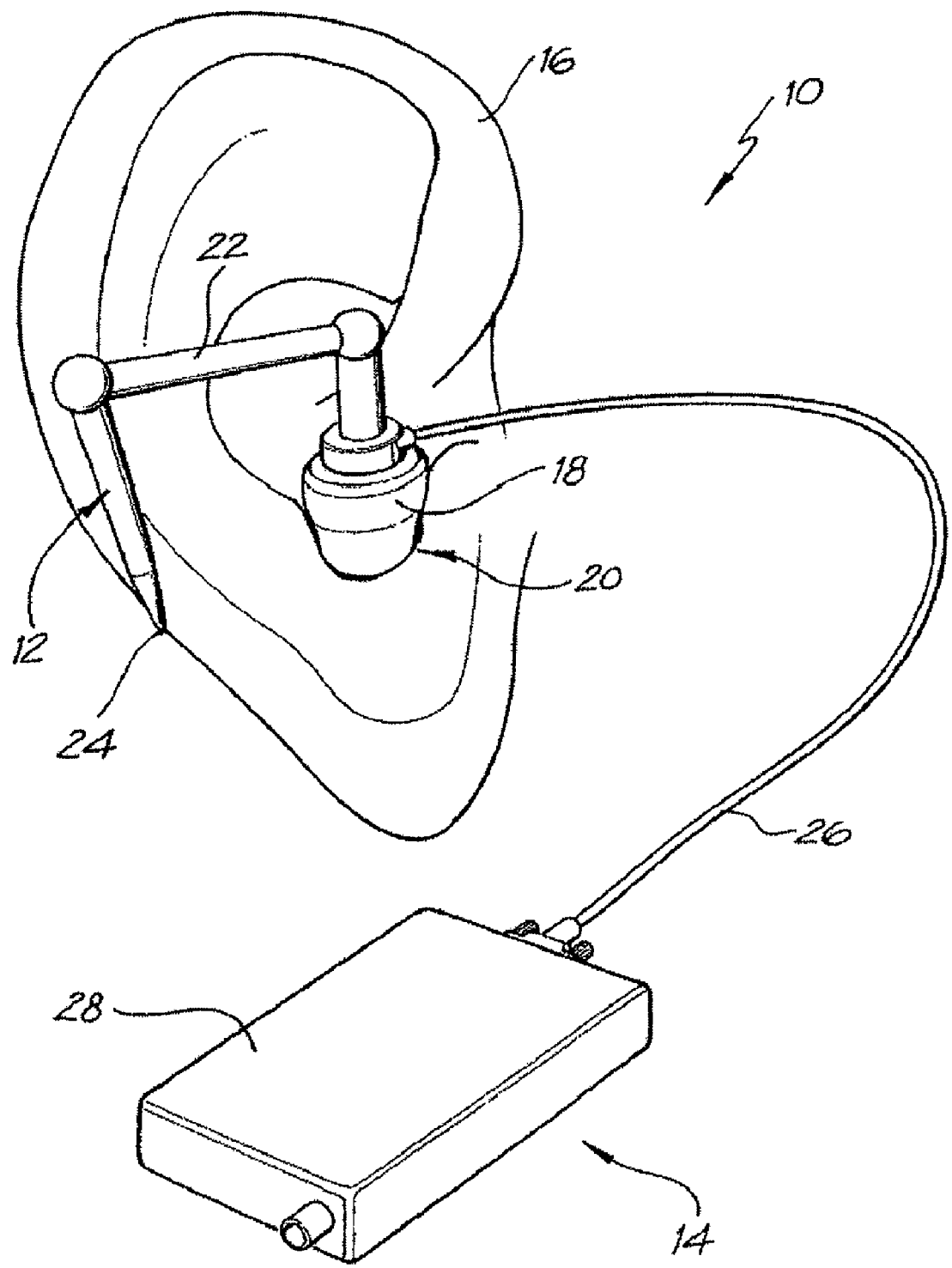

GENERATION OF CUSTOMISED THREE DIMENSIONAL SOUND EFFECTS FOR INDIVIDUALS

RELATED APPLICATIONS

This application is a continuation of prior application Ser. No. 10/181,648, filed Dec. 12, 2002, which is the national stage filing under 35 U.S.C. 371 of International Application PCT/AU01/00038, filed on Jan. 16, 2001, which claims the benefit of Australian Patent Application PQ 5140, filed on Jan. 17, 2000, all of which are herein incorporated by reference in their entirety.

FIELD OF THE INVENTION

This invention relates to the customisation of the processes of synthesis and generation of three dimensional sound effects for individual listeners. More particularly, the invention relates to a method of, and a system for, customising spatial hearing in virtual auditory space (AS) for individual listeners and to a measuring device for use in customising spatial hearing in VAS for individual listeners.

BACKGROUND TO THE INVENTION

The prior art discloses various methods for the synthesis and generation of three dimensional sound effects. All of these methods involve the use and synthesis of head-related transfer functions (HRTFs). These HRTFs define exactly the acoustic filtering characteristics of an individuals external auditory periphery, consisting primarily of the torso, shoulders, head, neck, and external ears, (hereinafter referred to as the external 'auditory periphery'). The HRTFs are dependent on the precise shape and geometry of the external auditory periphery. As this varies from individual to individual, each individual and each spatial direction around the individual requires its own unique HRTF for the left ear and for the right ear in order to accurately synthesis virtual auditory space (VAS), which refers to the electronic synthesis of spatial hearing in an artificial acoustic environment.

The prior art specifies HRTFs in both the time domain and in the frequency domain. Time domain descriptions of the HRTFs take the form of coefficients for a finite impulse response (FIR) filter, coefficients for an infinite impulse response (IIR) filter, or as sound samples. Frequency domain descriptions of HRTFs take the form of a complex-valued frequency response, a magnitude frequency response, or as frequency equalisation weights. The prior art also uses principal component analysis to compress the representation of HRTFs at single locations. The principal component analysis can be applied to either the time domain or the frequency domain representation of the HRTFs.

Some of the prior methods for the synthesis and generation of three dimensional sound effects do not use customised HRTFs, but use the same approximate HRTFs for all individuals. Approximate HRTFs are derived from a population average, from an acoustic mannequin or from an acoustic model of the acoustic filtering of the external auditory periphery. More particularly, some methods use a statistical means to compute approximate HRTFs as the population average of a set of several individuals' HRTFs, some methods use the approximate HRTFs provided by an acoustic mannequin, such as the KEMAR mannequin, the Brüel-Kjær mannequin, the Head Acoustic mannequin, or the like, while some methods determine an approximate HRTF from a standard set of parameter values for an acoustic model of the external auditory periphery.

Some of the prior methods for customising the process of synthesis and generation of three dimensional sound effects for individual listeners involve sending a person to an acoustic laboratory with the equipment required to acoustically record the HRTFs. A variation of this is taking a physical mould of the person's ears and then attaching the ear moulds to an acoustic mannequin and acoustically recording the HRTFs of the mannequin combined with the new ear moulds in the appropriate laboratory. The acoustic mannequins that are frequently used are the KEMAR mannequin, the Brüel-Kjær mannequin, or the Head Acoustic mannequin.

Other prior art methods for customising the process of synthesis and generation of three dimensional sound effects for individuals attempt to avoid the difficult acoustical measurements which are costly in both time and equipment. These methods may involve, for example, taking an optical scan of a person's head and then using image processing to produce an image suitable for computer simulation of acoustic wave propagation. Still other methods involve using a database of acoustically recorded HRTFs for a set of known listeners, searching the database for the HRTF that best matches an unknown listener by playing test sounds filtered with the HRTFs in the database to the unknown listener and then asking the unknown listener questions about the quality and location of the synthesized sound Another method, which uses a database of HRTFs, involves scaling the frequency axis of the HRTFs in the database in order to customise a set of HRTFs for the individual listener. It has not yet been reported whether there exists a means for determining the scaling parameter. Yet another method involves generating a set of HRTFs using electro-acoustic simulation of the individual's external auditory periphery.

All of these prior art methods have disadvantages associated with them, with the primary disadvantage being that none of them, except for the acoustical measurements in the laboratory and the computer simulation of the acoustic wave equation based on an optical image, provide a reliable and workable method with which to relate the physical morphology of the individual listener's external auditory periphery to a usable set of HRTFs with any controllable degree of accuracy. The acoustical measurement process is cumbersome, costly and inefficient. The computer simulation of the acoustic wave equation requires an optical image which requires such high definition that a mould of the ear usually has to be taken for the optical imaging. This usually ends up costing as much in time and equipment as the acoustical measurements in the first place. All of the other methods which do not involve acoustical measurements have uncontrollable errors Certain of the prior art methods do not produce customised HRTFs. Instead they use the same approximate HRTFs for all individual listeners. The first method using a database of HRTFs referred to above, while producing a set of "best match" HRTFs, requires the individual listener to listen to many different sounds filtered with other individual's HRTFs in the database in order to find the best match. This is time-consuming and imprecise. The second method which also uses a database of HRTFs referred to above, does not have a direct means to determine which HRTFs in the database should be used to apply a scaling of the frequency axis or to what value the scaling parameter should be set. An additional disadvantage for all of the known methods which use a database of HRTFs is that they do not have any procedure for improving the customisation to any reasonable degree of accuracy. Furthermore, the size of the database would have to be inordinately large to achieve high-fidelity. The electro-acoustic method is difficult because it requires estimating and setting parameters for electronic circuits such as resonators, filters, adders, and time-delay circuits and is not reliable.

Certain of the prior art methods described above have disadvantages in that they do not provide a single means for easily producing varying degrees of customisation of HRTFs for individual listeners. Such a varying degree of customisation is likely to be valuable in developing and applying VAS technology to its different areas of application.

Other of the prior art methods described above have disadvantages in their data storage and compression of HRTF data across a population of people. A single device suitable for use by many different individual listeners typically requires a large database of HRTFs.

Further, some of the prior art methods described above have disadvantages in the inefficiency of their searching procedure for finding the best set of customised HRTFs for an individual listener.

Still other of the prior art methods described above have disadvantages in not having a direct procedure for producing customised HRTFs that do not require using or searching a database of HRTFs.

Finally, some of the prior art methods described above have disadvantages in that they do not have a means to reduce the amount of acoustical or optical measurements required for customising a set of HRTFs for an individual listener, while maintaining high-fidelity in the HRTFs. Such a reduction in the amount of measurements required is valuable because it reduces the amount of time required for active participation of the individual listener during the acoustical or optical measurement process. Some of the prior art methods using acoustical measurements do not have a means for systematically reducing the number of locations at which HRTFs are to be measured. Some of the prior art methods using optical measurement techniques do not have a means for reducing the details of the optical image because they must rely on a computer simulation of acoustic wave propagation.

SUMMARY OF THE INVENTION

According to a first aspect of the invention, there is provided a method for customising spatial hearing in virtual auditory space (VAS) for individual listeners, the method including the steps of determining the morphology of an individual listener's external auditory periphery;

producing a head related transfer function (HRTF) for the individual listener from the morphology of the individual listener's external auditory periphery by applying a generative statistical model; and using the HRTF in the generation of spatial hearing in VAS.

In this specification, unless the context clearly indicates otherwise, the term "morphology" is to be understood in a broad sense as applying to any physical characteristic of an individual listener's external auditory periphery which is measurable directly or indirectly and various methods may be used for measuring morphology.

Thus, the method may include measuring a small number of HRTFs for a few specific locations and using these and the morphological determination of the individual listener's external auditory periphery in the generative statistical model to produce a customised set of HRTFs for use in the generation of spatial hearing in VAS for the individual listener.

Instead, in another embodiment of the invention, the method may include creating a database of HRTFs for a population of people and also creating a matching database of morphological measurements of the population of people. Preferably, both databases are temporarily created.

The method of generating the generative statistical database may include concatenating, for each individual listener in the population, the mathematical description of the individual listener's data into a single vector of numbers;

combining the various single vectors of a number of individual listeners into a set of vectors; and applying statistical analysis to the set of vectors to compress the data across the population of individual listeners. It will be appreciated that the data may be HRTFs of the individual listener for a fixed and finite set of locations which are then concatenated into a single large vector of numbers spanning several different locations. Instead, or in addition, the data may relate to morphology measurements of a fixed and finite set of morphological landmarks of the external auditory periphery of the individual listener which are then concatenated into a single large vector of numbers.

The method may include applying statistical analysis such as, for example, multivariable linear regression analysis to obtain a mathematical functional relationship between the HRTF data collected for the population of people and the morphological landmark data collected for the population of people. Instead, the method may include using a neural network to obtain a mathematical functional relationship between the HRTF data collected for the population of people and the morphological landmark data collected for the population of people.

The method may thus include, by means of a predetermined mathematical technique performed on data in the database, generating the generative statistical model from which any individual listener's HRTFs for any direction in space can be calculated completely independently of either database and irrespective of whether or not that individual listener is included in either database. The mathematical technique may be selected from the group comprising principal component analysis, independent component analysis, multivariable statistical regression analysis, spherical interpolation methods, neural networks and a combination of the aforegoing.

Irrespective of the embodiment, the method may include determining the morphology of the individual listener's external auditory periphery by measuring the physical shape of the external auditory periphery. The method may thus include measuring and recording relative Cartesian coordinates of the external auditory periphery by manipulating a measuring means relative to a reference point defined by a reference-defining means.

The method may include defining a reference plane for measuring purposes and for determining the Cartesian coordinates. The reference plane may be defined or mapped using three morphological landmarks of a person's head. These landmarks may be a left ear canal, a right ear canal and a bridge or tip of the nose. Then, the x and y axes may lie in the plane of these three landmarks with the z axis being perpendicular to this plane.

The method may include storing the determined morphology in a data storage device. Instead, the method may include transmitting the determined morphology as a bit stream.

According to a second aspect of the invention there is provided a method for producing customised spatial hearing in VAS for individual listeners, the method including the steps of (a) applying a method of compressing a mathematical description of a set of predetermined data across a population of different people to the set of predetermined data across a population of different people to produce customised data for the individual listener;

(b) modifying the values of statistical coefficients that are used to represent people in the database;

(c) creating spatialised test sounds in VAS at test locations using the modified data that have been produced by using the modified values of the coefficients;

(d) having the individual listener identify the perceived optimal test sounds using the modified values of the coefficients based on listening comparisons of the test sounds; and (e) using the optimal modified values of the coefficients to generate customised HRTFs for the individual listener.

Step (a) may include concatenating, for each individual listener in the population, the mathematical description of the individual listener's data into a single vector of numbers;

combining the various single vectors of a number of individual listeners into a set of vectors; and applying statistical analysis to the set of vectors to compress the original data across the population of individual listeners.

The data may be HRTFs of an individual listener for various single locations which are then concatenated into a single large vector of numbers spanning several different locations. Instead, or in addition, the data may relate to external auditory periphery morphology measurements of the individual listener.

According to a third aspect of the invention, there is provided a system for customising spatial hearing in VAS for individual listeners, the system including a device for measuring the physical dimensions of the morphology of an individual listener's external auditory periphery;

a processing means in communication with the device, the processing means using a generative statistical model to produce customised HRTFs for the individual listener; and a data storage and transmission means in communication with the processing means for incorporating the customised HRTFs in the generation of spatial hearing in VAS for the individual listener.

According to a fourth aspect of the invention, there is provided a system for customising spatial hearing in VAS for individual listeners, the system including a reference-defining means insertable into a person's ear;

a measuring means pivotally attached to the reference-defining means to be movable omni-directionally with respect to the reference-defining means for performing measurements of an individual listener's external auditory periphery;

a processing means in communication with the device for producing customised HRTFs for the individual listener; and a data storage and transmission means in communication with the processing means for incorporating the customised HRTFs in the generation of spatial hearing in VAS for the individual listener.

In this fourth aspect of the invention, the DPU may also apply a generative statistical model to produce the customised HRTFs.

The reference-defining means may be in the form of a base which, in use, is inserted into an auditory canal of the individual listener's ear.

The measuring means may be in the form of an arm, a tip of which is omni-directionally displaceable relative to the base The processing means may be a digital processing unit (DPU). The DPU may be selected from the group comprising a digital signal processing chip, a programmable interface controller, a field programmable gate array and a custom application specific integrated circuit.

The DPU may be programmed to compute at least one of HRTF filter coefficients and HRTF spectral weights.

The system may include a digital storage device for saving an output from the DPU electronically. The storage device may be selected from the group comprising an electrically erasable programmable read-only memory, a random access memory, a disk and a smart card. Instead, an output from the DPU may be sent to another device as a bit stream.

In one embodiment of the invention, the DPU may contain a small number of HRTFs for a few specific locations and may use these and the morphological measurements of the individual listener's external auditory periphery in the generative statistical model to produce a customised set of HRTFs for use in the generation of spatial hearing in VAS for the individual listener.

In another embodiment of the invention, the DPU may include a database of HRTFs for a population of people and also a matching database of morphological measurements of the population of people. The DPU may use a predetermined mathematical technique on data in the databases for generating the generative statistical model from which any individual listener's HRTFs for any direction in space can be calculated completely independently of either database and irrespective of whether or not that individual listener is included in either database. The mathematical technique may be selected from the group comprising principal component analysis, independent component analysis, multivariable statistical regression analysis, spherical interpolation methods, neural networks and a combination of the aforegoing.

According to a fifth aspect of the invention there is provided a system for customising spatial hearing in VAS for individual listeners, the system including a processing means for applying a generative statistical model to produce customised HRTFs for an individual listener and for modifying the values of the statistical coefficients that are used to generate the HRTFs;

a generating means for generating spatialised test sounds in VAS at test locations using the generated HRTFs;

a signaling means for having the individual listener signal an identification of the perceived optimal test sounds using the modified values of the coefficients; and a data storage and transmission means for incorporating the customised HRTFs using the optimal modified values of the coefficients in the generation of spatial hearing in VAS for the individual listener.

The processing means may compress the mathematical description of an individual listener's set of predetermined data across a population of different individual listeners.

Accordingly, the processing means may concatenate, for each individual listener in the population, the mathematical description of the data into a single vector of numbers;

combine the various single vectors of a number of individual listeners into a set of vectors; and apply statistical analysis to the set of vectors for producing a compressed database comprising the original data across the population of individual listeners.

The data may be HRTFs of an individual listener for various single locations which are then concatenated into a single vector of numbers spanning several different locations. In addition, or instead, the data may relate to external auditory periphery morphology measurements of the individual listener.

According to a sixth aspect of the invention there is provided a component for customising spatial hearing in VAS for individual listeners, the component including a reference-defining means insertable into an individual listener's ear; and a measuring means pivotally attached to the reference-defining means to be movable omni-directionally with respect to the reference-defining means for performing measurements of an individual listener's external auditory periphery.

The component, which will hereinafter be referred to for the sake of simplicity as a ruler, may be in the form of a small, segmented robotic device.

The reference-defining means may be in the form of a base which, in use, is inserted into an auditory canal of the individual listener's ear.

The primary feature of the ruler is to record the relative Cartesian (x,y,z) coordinates of the position of the measuring means relative to the base. Thus, the measuring means may be in the form of an arm, a tip of which is omni-directionally displaceable relative to the base.

BRIEF DESCRIPTION OF THE DRAWINGS

The invention is now described by way of example with reference to the accompanying drawing which shows, schematically, a system, in accordance with the invention, for customising the synthesis and generation of spatial hearing in VAS for individual listeners.

DETAILED DESCRIPTION OF THE DRAWINGS

In the drawing, reference numeral 10 generally designates a system, in accordance with the invention, for customising the synthesis and generation of spatial hearing in VAS for individual listeners or, for the sake of brevity, individuals. The system 10 includes a measuring means or ruler 12, also in accordance with the invention, and a processing means 14 to which the ruler 12 is connected.

The ruler 12 is used for measuring various physical dimensions of the morphology of an individual or person's external auditory periphery 16 and the ruler 12 is shown in situ. The ruler 12 comprises a reference-defining means or base 18 insertable into an ear canal 20 of the person's ear. A robotic measuring arm 22 extends from the base 18 and has a measuring tip 24. The purpose of the ruler 12 is to record the Cartesian (x,y,z) coordinates of the tip 24 relative to the base 18. To enable these measurements to be effected, a reference plane is defined using various morphological characteristics of the person's head. More particularly, a plane is defined by the ear canals of the person's right and left ears and the bridge of the nose. The x and y axes then lie in the plane of these three landmarks with the z axis extending perpendicularly to this plane. Accordingly, by suitable manipulation of the robotic arm 22, the tip 24 can be positioned at desired locations on the person's external auditory periphery 16 to enable the morphological measurements of the person's external auditory periphery 16 to be effected.

The ruler 12, as described above, is electrically connected via a lead 26 to the processing means 14. The processing means 14 includes a digital processing unit (DPU) 28. The (DPU) 28 can take various forms and can be a digital signal processing chip, a programmable interface controller, a field programmable gate array or a custom application-specific integrated circuit. The DPU 28 is also programmed to compute either HRTF filter coefficients or HRTF spectral weights.

The morphology of an individual's external auditory periphery (including outer ear shape and concha shape) is "individualised" or unique in the same sense that thumb print-marks are individualised. Associated with the individualised morphology, every individual has different peripheral auditory filtering characteristics or HRTFs. In general, it is an extremely difficult task to measure the HRTFs and an anechoic room, a robotic loudspeaker system, head-tracking gear and the immobility of the person is required for a predetermined period of time, for example, half an hour. Therefore, to date, it has only been possible to measure the HRTFs using special equipment and personnel.

A few laboratories such as the Auditory Neuroscience Laboratory of the University of Sydney, Australia, have a population database of HRTFs along with a matching database of morphological measurements for the external auditory peripheries of the individuals in their population database of HRTFs. In order to relate the morphology of an individual's external auditory periphery to the filtering characteristics described by the individual's HRTFs, basic principles of statistical shape analysis can be applied: (1) given population databases, as described above, of sufficient size, it is theoretically possible to statistically relate the differences between different individual's HRTFs to the differences between the morphology of their external auditory periphery; (2) the morphological shape of the individual's external auditory periphery may be represented mathematically by the geometry described by their morphological landmarks. Importantly, statistical shape analysis, as described here, is not being used to mathematically solve an acoustic wave-propagation problem, but only to relate differences in morphology to differences in acoustic filtering properties. In order to mathematically describe the morphology of an individual's external auditory periphery, several morphological landmarks of the external auditory periphery may be identified. Some of these landmarks are: (1) the join of the ear lobe and head; (2) the join of the ear helix and head; (3) the join of the crus helix and cymiba; (4) the tragal notch; (5) the crus helix; (6) the antihelix; (7) the upper tragal bump; (8) the lower tragal bump; (9) the antitragal bump; (10) entrance of the auditory canal; (11) bridge or tip of the nose; (12) chin; (13) shoulder.

Using mathematical techniques and the two databases described above, a generative statistical model of an individual's HRTFs can be constructed based upon the morphology of the individual's external auditory periphery such that high-fidelity and individualised spatial hearing in VAS is possible for any individual independent of whether the individual is included or not included in the databases.

A brief description of the steps involved in the mathematical technique follows. In a first step, principal components analysis is applied to compress the magnitude frequency response of every HRTF for various single locations in the database. As a second step, the mathematical description of each individual's HRTFs for the various single locations are concatenated to produce a high dimensional vector of numbers describing the HRTFs across many locations for that individual. As a third step, principal component analysis is applied for the second time to the collection, across the population of individuals, of high dimensional vectors of numbers derived in the second step. The principal component analysis in the third step is calculated using the computational method known as Expectation-Maximisation. As a fourth step, the Cartesian coordinates of the morphological landmarks for different individuals are transformed so that all landmarks are described with respect to the same relative global coordinate system. As a fifth step, the transformed Cartesian coordinates for each individual's morphological landmarks are concatenated to produce a vector of numbers including coordinates for all of the different landmarks. As a sixth step, principal component analysis is applied to the collection, across the population of individuals, to the vector of numbers calculated in the fifth step. As a seventh step, multivariable statistical regression analysis is applied to derive a functional relationship between the principal component coefficients calculated in the third step and the principal component coefficients calculated in the sixth step. Spatial interpolation across a set of HRTFs (eg., using a spherical thin-plate spline) is an optional step that may be embedded into the algorithm described above.

The functional relationship described above is used to generate, by means of the DPU 28, HRTFs at any location for any individual given an encoding of the individual's morphological measurements.

It is possible to conduct an experimental study of how the morphological variation of different individuals' external auditory peripheries affect their perception and localisation of broadband noise. These experiments have been made possible because of the ability to perform principal components analysis on the high-dimensional vector of numbers as described above. A surprising result of the experiments indicate that only approximately one half of the morphological variation in different individuals' external auditory peripheries need be accounted for in a generative statistical model to produce high-fidelity HRTFs for use in spatial hearing in VAS. As a result of these experiments, it can be concluded that a generative statistical model of HRTFs based upon the morphology of an individual's external auditory periphery is able to produce high-fidelity VAS. The generative statistical model indicates that the shape of an individual's external auditory periphery accounts for a large proportion of the variance seen in the HRTFs across a population of people.

The output from the DPU 28 can be in several arithmetically different forms, eg., FIR filter coefficients. IIR filter coefficients, frequency equalisation weights and digitally stored using several different forms of digital memory, such as EEPROM, RAM, disk, smart card, or the like. Instead of storing the output, it can be packaged as an output stream or bit stream using any of the standard interface protocols.

Hence, once the morphological measurements of the external auditory periphery have been measured by the ruler 12, these measurements are transmitted to the DPU 28 where they are processed to generate the HRTFs. A generative statistical model is applied to the morphological measurements to generate the HRTFs with a degree of fidelity that is determined and controlled by the precision and detail of the morphological measurements.

It is an advantage of the invention that acoustical measurements are avoided, that a computational solution of acoustic wave-propagation is avoided, and that large databases of HRTFs are avoided in the implementation. Furthermore, the computational and memory requirements are minimal because search methods for optimal HRTFs have been obviated by the construction of a generative statistical model, and trial and error is avoided. An additional advantage of the method is that the precision and detail of the morphological measurement can easily be adjusted to match the degree of fidelity desired in the rendering of an individual's VAS. For example, low level acoustic fidelity in the rendering of VAS may only require a few qualitative morphological measurements of an individual's external auditory periphery.

A major advantage of the method described is that it can produce an individualised HRTF directly from morphological measurements of an individual's external auditory periphery. Hence, it will be appreciated that the advantage of this is its simplicity, cost effectiveness, speed and directness. It is simple because a small number of ruler measurements are required and is inexpensive because the measuring means or ruler 12 can be inexpensively implemented. The speed with which it can be done arises from the arithmetical simplicity of the generative statistical model from which the required HRTFs can be generated by the DPU 28 using the morphological measurements. Also, it is direct because it avoids having a listener search for a best matching set of HRTFs.

The applicant envisages that the invention will have a wide range of applications. These would include, for example:

In the entertainment and leisure industry in the form of computer games exploiting virtual reality, in portable musical devices to generate a highly realistic listening environment over headphones; in movies where the spatial surround characteristics of the sound field can be greatly improved over traditional multi-loudspeaker placements in the cinema or home theatre.

In communications systems that involve multiple streams of auditory information delivered over headphones. The ability to separate out separate conversations is very greatly enhanced when the sources are placed in different spatial locations. This would also apply to teleconferencing and video conferencing.

In guidance and alerting systems where for instance the presence and trajectory of potential collision objects that cannot be visually appreciated can be mapped into auditory icons which occupy different locations in space.

In teleorobotics where the control of remote devices involves a virtual reality interface. The utility of such control systems is dependent on the capability of the interface to induce the sense of 'telepresence' in the operator for which the auditory system plays a key psychophysical role.

In the remapping of various types of information into the auditory spatial domain. For example, in conditions such as a flight cockpit where there is considerable mission critical information presented visually a reduction of visual overload by mapping information into the auditory spatial domain such as auditory horizon indicators.

Many of the mission critical applications above require precise rendering of virtual auditory space (eg. collision avoidance systems) which require that the HRTFs of the operator/listener need to be very accurately determined. The invention described above provides this accuracy using a means which will allow a much greater exploitation of these kinds of technologies than prior methods of direct measurement of the individualised HRTFs of individual operator/listeners.

It will be appreciated by persons skilled in the art that numerous variations and/or modifications may be made to the invention as shown in the specific embodiments Without departing from the spirit or scope of the invention as broadly described. The present embodiments are, therefore, to be considered in all respects as illustrative and not restrictive.

The invention claimed is:

1. A method for customizing spatial hearing in virtual auditory space (VAS) for individual listeners, the method including the steps of
creating a database of head related transfer functions (HRTFs) for a population of people;
measuring a small number of HRTFs for a predetermined number of specific locations for an individual listener;
by means of a predetermined mathematical technique performed on data in the database and the measured HRTFs, generating a generative statistical model from which any individual listener's HRTFs for any direction in space can be calculated completely independently of the database and irrespective of whether or not that individual listener is included in the database;

producing a set of customized head related transfer functions for the individual listener by applying the generative statistical model; and using the produced HRTFs in the generation of spatial hearing in VAS.

2. The method of claim 1 in which generating the generative statistical database includes concatenating, for each individual listener in the population, a mathematical description of the individual listener's data into a single vector of numbers;

combining the various single vectors of a number of individual listeners into a set of vectors; and applying statistical analysis to the set of vectors to compress the data across the population of individual listeners.

3. The method of claim 2 in which the data are HRTFs of the individual listener for a fixed and finite set of locations which are then concatenated into a single large vector of numbers spanning several different locations.

4. The method of claim 2 in which the data includes morphology measurements of a fixed and finite set of morphological landmarks of the individual listener which are then concatenated into a single large vector of numbers.

5. The method of claim 4 which includes applying statistical analysis to obtain a mathematical functional relationship between the HRTF data collected for the population of people and morphological landmark data collected for the population of people.

6. The method of claim 4 which includes using a neural network to obtain a mathematical functional relationship between the HRTF data collected for the population of people and morphological landmark data collected for the population of people.

7. The method of claim 1 which includes selecting the mathematical technique from the group consisting of principal component analysis, independent component analysis, multivariable statistical regression analysis, spherical interpolation methods and neural networks.

8. The method of claim 4 which includes measuring and recording relative Cartesian coordinates of the morphological landmarks of the individual listener by manipulating a measuring means relative to a reference point defined by a reference-defining means.

9. The method of claim 8 which includes defining a reference plane for measuring purposes and for determining the Cartesian coordinates.

10. The method of claim 9 which includes defining the reference plane by using at least three morphological features of the individual listener's head.

11. The method of claim 1 which includes storing the produced HRTFs in a data storage device.

12. The method of claim 1 which includes transmitting the produced HRTFs as a bit stream.

13. A system for customizing spatial hearing in VAS for individual listeners, the system including a processing means including a database of HRTFs for a population of people and data relating to a small number of HRTFs for a predetermined number of specific locations for an individual listener and the processing means using a predetermined mathematical technique on data in the database for generating a generative statistical model from which any individual listener's HRTFs for any direction in space can be calculated completely independently of the database and irrespective of whether or not that individual listener is included in the database, the generative statistical model being used by the processing means to produce customized HRTFs for the individual listener; and a data storage and transmission means in communication with the processing means for incorporating the customized HRTFs in the generation of spatial hearing in VAS for the individual listener.

14. The system of claim 13 in which the processing means is a digital processing unit (DPU).

15. The system of claim 14 in which the DPU is selected from the group consisting of a digital signal processing chip, a programmable interface controller, a field programmable gate array and a custom application specific integrated circuit.

16. The system of claim 13 in which the DPU is programmed to compute at least one of HRTF filter coefficients and HRTF spectral weights.

17. The system of claim 14 which includes a digital storage device for saving an output from the DPU electronically.

18. The system of claim 17 in which the storage device is selected from the group consisting of an electrically erasable programmable read-only memory, a random access memory, a disk and a smart card.

19. The system of claim 14 in which the DPU is operable to send an output from the DPU to another device as a bit stream.

20. The system of claim 13 in which the mathematical technique is selected from the group consisting of principal component analysis, independent component analysis, multivariable statistical regression analysis, spherical interpolation methods and neural networks.

21. The system of claim 13 in which the data includes morphology measurements of a fixed and finite set of morphological landmarks of the individual listener which are then concatenated into a single large vector of numbers.

* * * * *